United States Patent [19]
Cooper

[11] 3,985,178
[45] Oct. 12, 1976

[54] PRECISION INVESTMENT CASTING APPARATUS WITH RESERVOIR BLOCKS

[76] Inventor: Abraham J. Cooper, Box 321, Pomona, N.Y. 10970

[22] Filed: May 1, 1975

[21] Appl. No.: 573,400

[52] U.S. Cl. .............................. 164/237; 164/244; 164/246; 164/DIG. 4
[51] Int. Cl.² ........................................... B22C 7/02
[58] Field of Search .............. 164/244, 246, DIG. 4, 164/237, 249

[56] References Cited
UNITED STATES PATENTS

| | | |
|---|---|---|
| 3,340,923 | 9/1967 | Benfield .............................. 164/244 |
| 3,610,317 | 10/1971 | Benfield et al. .................. 164/249 X |
| 3,648,760 | 3/1972 | Cooper .............................. 164/244 |
| 3,830,285 | 8/1974 | Schrader ............................ 164/249 |

Primary Examiner—Robert D. Baldwin
Attorney, Agent, or Firm—Albert F. Kronman

[57] ABSTRACT

Precision investment casting of small parts with fine detail and free of air inclusions is achieved by the use of flat sided blocks of a relatively high melting point plastic material received upon elongated tubes or rods of the same or similar material. The shape and size of the blocks permit a large number of small parts to be cast at the same time and provide reservoirs for the molten casting metal close adjacent the casting cavity.

7 Claims, 11 Drawing Figures

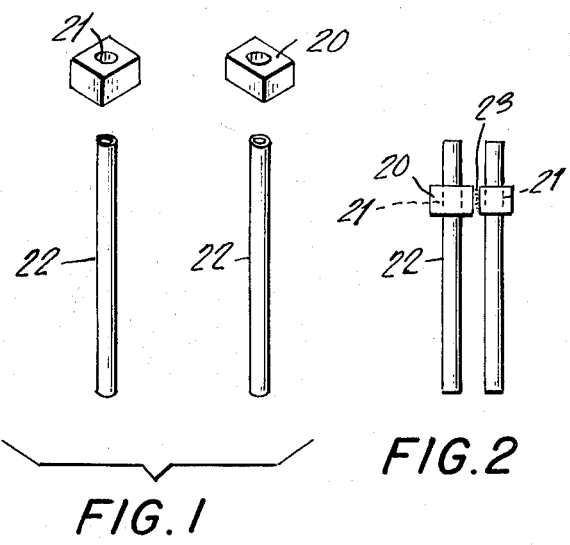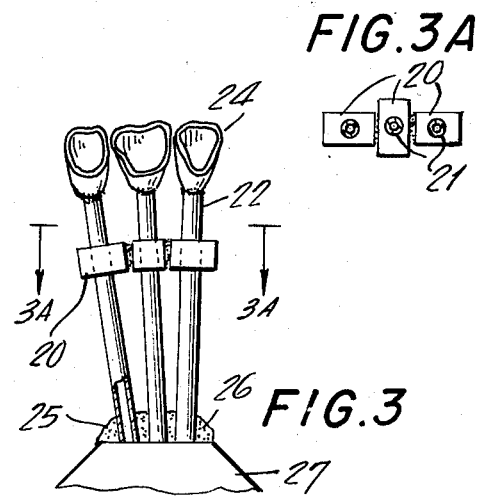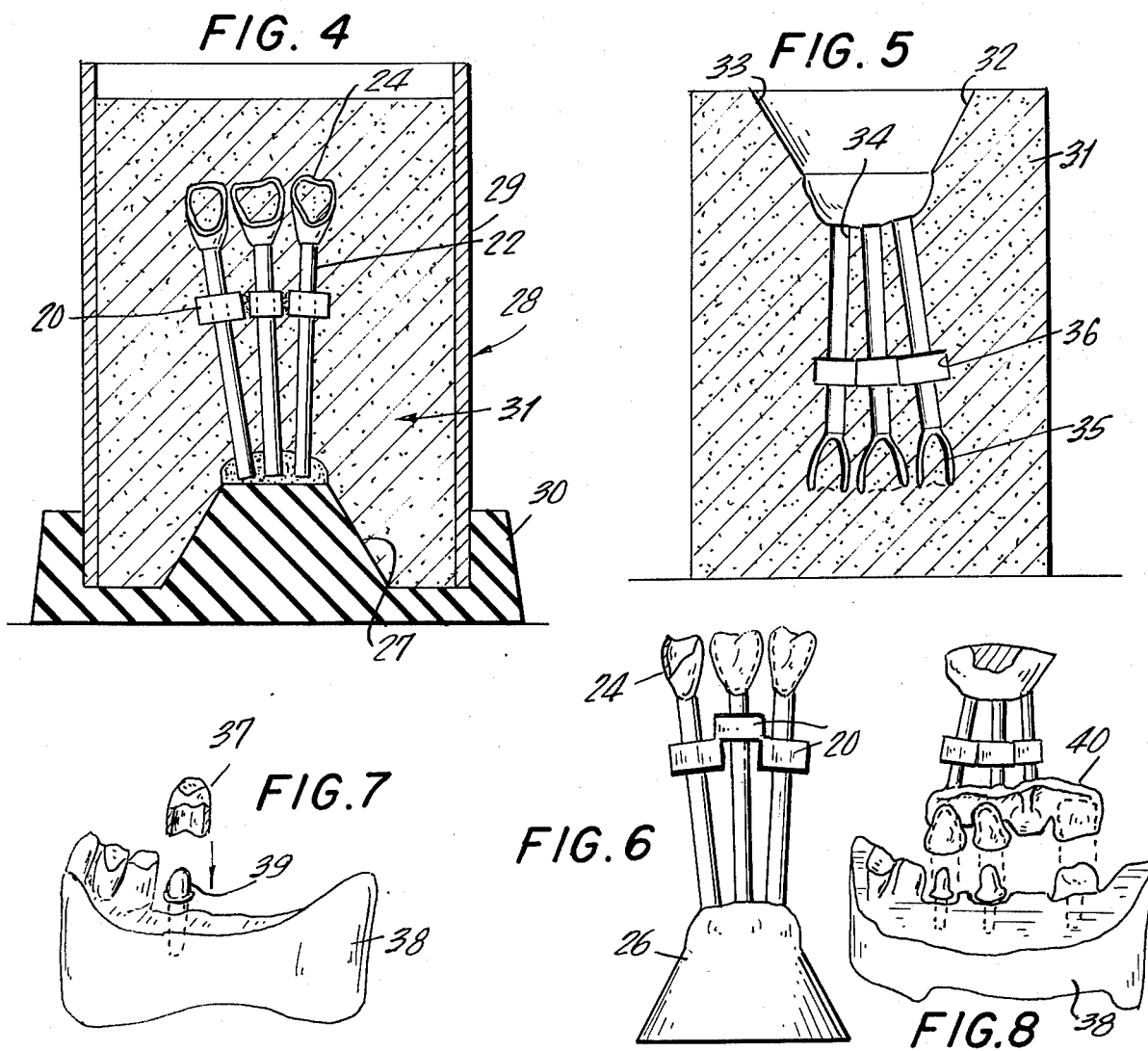

PRECISION INVESTMENT CASTING APPARATUS WITH RESERVOIR BLOCKS

BACKGROUND OF THE INVENTION

The casting of small parts such as dental restorations by the lost wax method is well-known. In order to produce satisfactory castings by this method it is often necessary to provide a reservoir of molten metal to compensate for shrinkage of the cast material as it cools. In addition, the additional metal insures that there are no voids such as gas or air bubbles in the casting cavity as the metal solidifies.

Where the parts to be cast are large or where only one part is desired, a single reservoir of substantial size, usually at the entrance or funnel of the investment material, will be adequate. Casting a plurality of small parts, however, requires that the reservoirs be placed close to the casting cavity.

Since the time necessary to produce a mold for lost wax casting is substantial it becomes uneconomic to cast single parts. Morever, it is highly desirable to cast as many parts as possible in the same casting operation.

Accordingly, it is an object of the present invention to provide apparatus which will facilitate the simultaneous, high quality casting of a plurality of small parts such as dental restorations.

Another object of the present invention is to provide apparatus for the casting of small parts which lends itself to a wide variety of casting requirements.

A further object of the present invention is to increase the number of small parts which may be cast in a single casting operation.

Other objects and features of the present invention will become apparent from the following description in which the parts to be cast are small dental restorations. It will be understood, however, that other small items such as, rings, buttons, settings, etc. may be cast in the hereinafter described manner without departing from the spirit of the present invention.

SUMMARY

The simultaneous, high quality casting of a plurality of small parts using the lost wax method is achieved by the use of several small substantially rectangular plastic blocks which are provided with a transverse bore. The blocks are longer than they are wide and freely fit upon elongated plastic sprue pins. Small wax patterns of the parts to be cast (such as dental crowns) are secured to the ends of the sprue pins by the application of wax and the blocks slipped over the pins. An arrangement of supported patterns closely adjacent each other but spaced by the blocks in then secured together by a relatively high melting point wax.

The assembly is secured to a dome shaped base and placed within a flask. The flask is filled with investment material which is allowed to harden around the patterns and their suporting structures. The investment is then heated, whereupon the plastic blocks, sprue pins and wax patterns melt and flow out of the investment material leaving a cavity for subsequent metal pouring.

DESCRIPTION OF THE DRAWINGS

In the accompanying drawings forming part hereof, like parts have been given identical reference numerals, in which drawings:

FIG. 1 is a somewhat exposed view in perspective of two plastic blocks and their associated sprue pins according to the present invention.

FIG. 2 is a view similar to FIG. 1 showing the blocks upon the sprue pins.

FIG. 3 is a view in side elevation, partly broken away, showing the manner in which the blocks and sprue pins are secured to wax patterns in an assembly for casting.

FIG. 3A is a sectional view taken on line 3A — 3A in FIG. 3 looking in the direction of the arrows.

FIG. 4 is a view in side elevation, partly broken away, of the pattern assembly within the investment filled flask.

FIG. 5 is a view in vertical section of the investment material and casting cavity following the removal of the blocks, sprue pins and wax patterns by heating.

FIG. 6 is a view in side elevation of the casting produced from the mold of FIG. 5.

FIG. 7 is a view in side elevation party exploded and broken away to show the manner in which the castings are placed upon a dental model.

FIG. 8 is a view similar to FIG. 7 but showing how a plurality of crowns may be cast in fixed relationship to conform to the requirements of a dental model.

GENERAL DESCRIPTION

Figure 9:
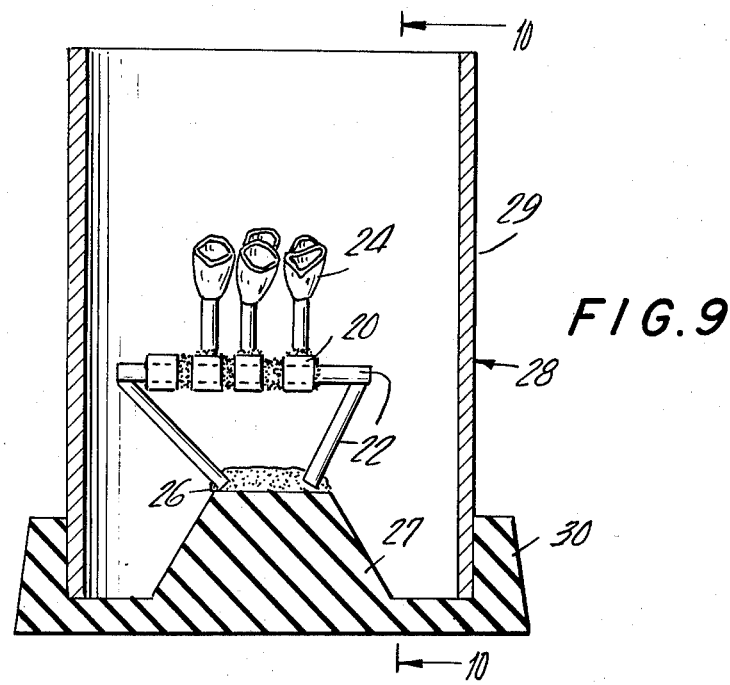
FIG. 9 is a view in side elevation showing another casting assembly according to the present invention.

Referring to the drawings, specifically to FIGS. 1 - 3, there is shown plastic blocks 20 made of polypropylene or similar material having a melting point higher than that of wax but lying within the range 350° - 900° F. The blocks 20 are rectangular in shape having a width somewhat narrower than their length. In addition, the blocks 20 are provided with a transverse bore 21 with a diameter sufficiently large to freely receive an elongated sprue pin 22. The sprue pin is preferably made of the same material as the block and may be either in the form of a tube or solid rod.

As shown in FIG. 2, the blocks 20 and their sprue pins 22 may be assembled and secured together by means of wax known as "sticky wax"[in the lost-wax casting art. The wax 23 has a lower melting point than the material of the blocks 20.

As shown in FIG. 3, the casting of small parts such as crowns 24 for dental restorations, the crowns to be cast, are first made in the form of wax patterns conforming in detail to the finished part. The wax patterns 24 are secured to the ends of the sprue pins 22 by means of wax. The blocks 20 are next slipped upon the pins 22 and their free ends 25 secured by means of wax 26 to a base 27, hereinafter more fully described. Since it is highly desirable to cast as many parts as possible, the crown patterns 24 are arranged in side-by-side relationship as closely as possible in the manner illustrated in FIG. 3. In order to economically arrange the crowns 24 the blocks 20 are oriented in the manner shown in FIG. 3a so that the narrower dimension of the block is used where the size of the crown or part to be cast permits. Alternately, the blocks 20 may be overlapped as shown in FIG. 6 to bring the crowns even closer together.

In casting small parts by the lost-wax process and particularly where the parts are of great detail and are thin walled, it is important that an adequate supply of molten metal be available within the pouring cavity and close adjacent that portion of the cavity represented by the part desired to be produced. This metal is made available by providing an enlarged reservoir of metal within the sprue of the casting. The blocks 20 serve this purpose in the present invention and are particularly suited for this function because they can be adjusted upon the sprue pins 22 to bring them into any desired position close to the cavity of the part to be made. It will be understood that as the casting metal cools it will shrink and often contain voids caused by gas bubbles or air inclusions. The metal in the reservoir is able to fill these voids and compensate for the shrinkage during the casting operation. While it is well-known to provide reservoirs for metal in the lost-wax casting process, such reservoirs are normally large and located at a distance from the position of the casting cavity represented by the article to be produced. In casting a large number of small parts as is the purpose of the present invention, a large reservoir is not possible and the provision of a plurality of small reservoirs such as results from the present assembly, serves to produce a high quality, void free end product.

Referring to FIG. 4, there is shown the next step in the casting process according to the present invention. In this step, the base 27 will be seen to be part of a flask 28 having a cylindrical body 29 and a flange 30 to receive the cylindrical body 29. With the assembly shown in FIG. 3 in place upon the base 27 and the flask body tightly secured within the flange 30, the flask is filled with investment material such as phosphate silica or any other well-known investment material. The investment material is then allowed to harden within the flask and around the assembled patterns, sprue pins, and blocks.

When the investment material is hard the flask 28 is removed and the hardened investment material 31 heated to a temperature of between 350° – 900° F. The plastic material of the sprue pins 22 and the blocks 20 as well as the wax contained within the investment material will then melt and flow out of the investment material leaving the cavity 32, best shown in FIG. 5. It will be seen that the cavity 32 now includes a funnel 33 into which molten metal can be poured, sprues 34 in communication with the part cavities 35 and reservoirs 36 close adjacent the cavities 35 where additional metal can be placed to improve the casting operation.

Casting may be accomplished by placing the mold in an agitator or centrifugal device, as is well-known in the art, for the purpose of forcing the metal into the entire cavity formed in the investment material 31.

After the casting operation, the investment material is broken away from the cooled metal and individual parts such as the crowns 37 shown in FIG. 7 can be cut off the casting and fitted into a dental model 38 in the manner shown in FIG. 7. The dental model 38 is provided with pins 39 corresponding to the prepared teeth of the patient. Precise fit and registration of the crowns 37 is achieved in the laboratory in this manner.

Referring to FIG. 8, there is shown another form of casting made in accordance with the present invention in which a plurality of dental restorations 40 are cast in accordance with the present invention and are maintained in their precise relationship with respect to each other and with respect to the model 38. This type of casting is particularly desirable where a bridge rather than an individual crown is required. In this use of the present invention, the elements of the bridge are kept together to form the bridge, thereby avoiding the need for subsequent soldering of the cast crowns.

Figure 10:
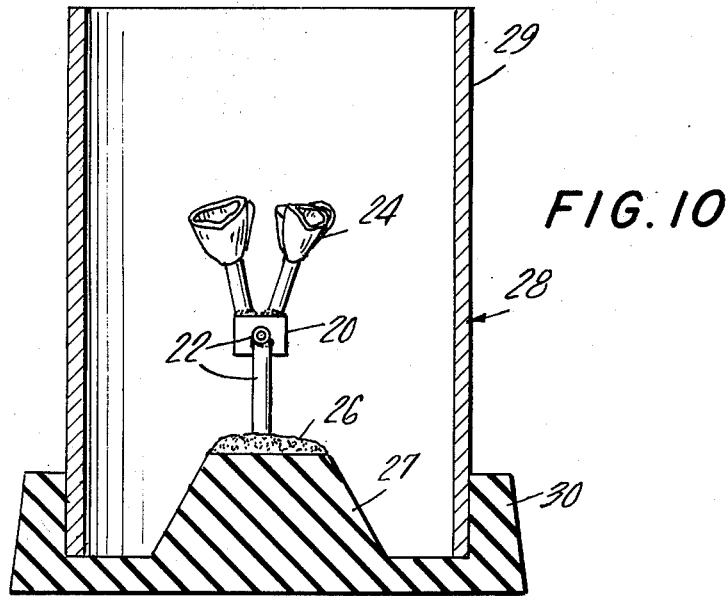
FIG. 10 is an end view of the assembly of FIG. 9.

Referring to FIGS. 9 and 10, it will be seen how a large number of small parts can be cast employing the blocks 20 and sprue pins 22 in the manner described above. In this form of the invention, two rows of patterns 24 are built upon a horizontal sprue pin 22 together with blocks 20 and having lateral sprue pins 22 for the purpose of feeding metal into the casting cavity from both ends of the assembly at the same time. This construction permits rapid application of the molten metal to the cavity despite the fact that there are a plurality of paths within the casting cavity.

From the foregoing it will be seen that there has been provided a highly desirable system consisting of blocks and sprues for the casting of a large number of small parts simultaneously and with great accuracy and uniformity. A wide variety of assemblies can be arranged by the operator in accordance with the requirements of the size and shape of the parts to be cast, which assemblies will be apparent to those skilled in the art.

Having fully described the invention, what is desired to be secured by Letters Patent is:

1. Precision investment casting apparatus for the simultaneous production of small parts comprising a plurality of transversely bored rectangular heat-destructible reservoir blocks, an elongated heat-destructible sprue pin freely receivable within each block bore, means to secure a pattern to the end of each sprue pin, means to secure each block to its respective sprue pin at a point adjacent but spaced from the pattern, flask means including a base to receive the free ends of the sprue pins and a hollow body around the said base to receive investment material.

2. Apparatus according to claim 1 in which the blocks have a width of lesser dimension than the length thereof.

3. Apparatus according to claim 1 in which the blocks and sprue pins have a melting point of between 350° to 900° F.

4. Apparatus according to claim 1 in which the blocks and sprue pins are made of polypropylene.

5. Apparatus according to claim 1 in which adjacent blocks are secured together by wax.

6. Apparatus according to claim 1 in which the blocks are received on and secured to transverse common sprue pin and at least two sprue pins with patterns are secured to and extend from each block.

7. Apparatus according to claim 6 in which the common sprue pin is connected to the base by additional sprue pins at each end of the common sprue pin.

* * * * *